(12) United States Patent
Becker

(10) Patent No.: US 9,254,225 B2
(45) Date of Patent: Feb. 9, 2016

(54) PUNCTAL PLUG INSERTER AND METHOD

(76) Inventor: Bruce B. Becker, Malibu, CA (US)

( * ) Notice: Subject to any disclaimer, the term of this patent is extended or adjusted under 35 U.S.C. 154(b) by 0 days.

(21) Appl. No.: 13/186,665

(22) Filed: Jul. 20, 2011

(65) Prior Publication Data

US 2013/0023837 A1 Jan. 24, 2013

(51) Int. Cl.
*A61F 9/00* (2006.01)
*A61F 9/007* (2006.01)

(52) U.S. Cl.
CPC .................................. *A61F 9/00772* (2013.01)

(58) Field of Classification Search
CPC ..... A61F 9/00; A61F 9/0017; A61F 9/00772; A61F 9/00781; A61B 17/12022; A61B 17/12099; A61B 17/12159
USPC ...................................................... 604/294, 8
See application file for complete search history.

(56) References Cited

U.S. PATENT DOCUMENTS

| | | | |
|---|---|---|---|
| 5,741,292 | A | 4/1998 | Mendius |
| 6,344,047 | B1 * | 2/2002 | Price et al. .................... 606/191 |
| 7,017,580 | B2 | 3/2006 | Prescott et al. |
| 7,846,124 | B2 | 12/2010 | Becker |
| 2005/0154399 | A1 * | 7/2005 | Weber et al. .................. 606/107 |
| 2005/0197614 | A1 | 9/2005 | Pritchard et al. |
| 2009/0105749 | A1 * | 4/2009 | de Juan et al. ................ 606/206 |
| 2011/0196317 | A1 * | 8/2011 | Lust et al. ..................... 604/290 |

FOREIGN PATENT DOCUMENTS

WO WO 03/041622 A3 5/2003

OTHER PUBLICATIONS

Second sheet of International Search Report for corresponding application PCT/US2012/047727.

* cited by examiner

*Primary Examiner* — Philip R Wiest
*Assistant Examiner* — Benjamin Klein
(74) *Attorney, Agent, or Firm* — Charmasson, Buchara & Leach, LLP

(57) ABSTRACT

A surgical tool for inserting a spile or plug into the punctal opening of a meatus such as a lacrimo-nasal canaliculus comprises an oblong, hollowed member shaped and dimensioned to be conveniently manipulated with one hand and having at one of its end a punctal opening and meatus-dilating shaft and, at the opposite end, a plug inserter. The dilating shaft has a cross-diameter substantially equal to the cross-diameter of the plug and is terminated by a conical spike. The inserter comprises a tip extending axially from the member and having, at its distal end, a cup whose internal geometry is commensurate with a cap at the proximal end of the plug. A penetration-resisting bearing surface is provided by the cup rim. The plug can be allowed to retract within the cup under the force of insertion. A steel wire running through the inserter has its distal end inserted into the cap of the plug. The wire can be axially withdrawn by unidirectionally pressing a button in order to release the plug after insertion into the meatus.

26 Claims, 6 Drawing Sheets

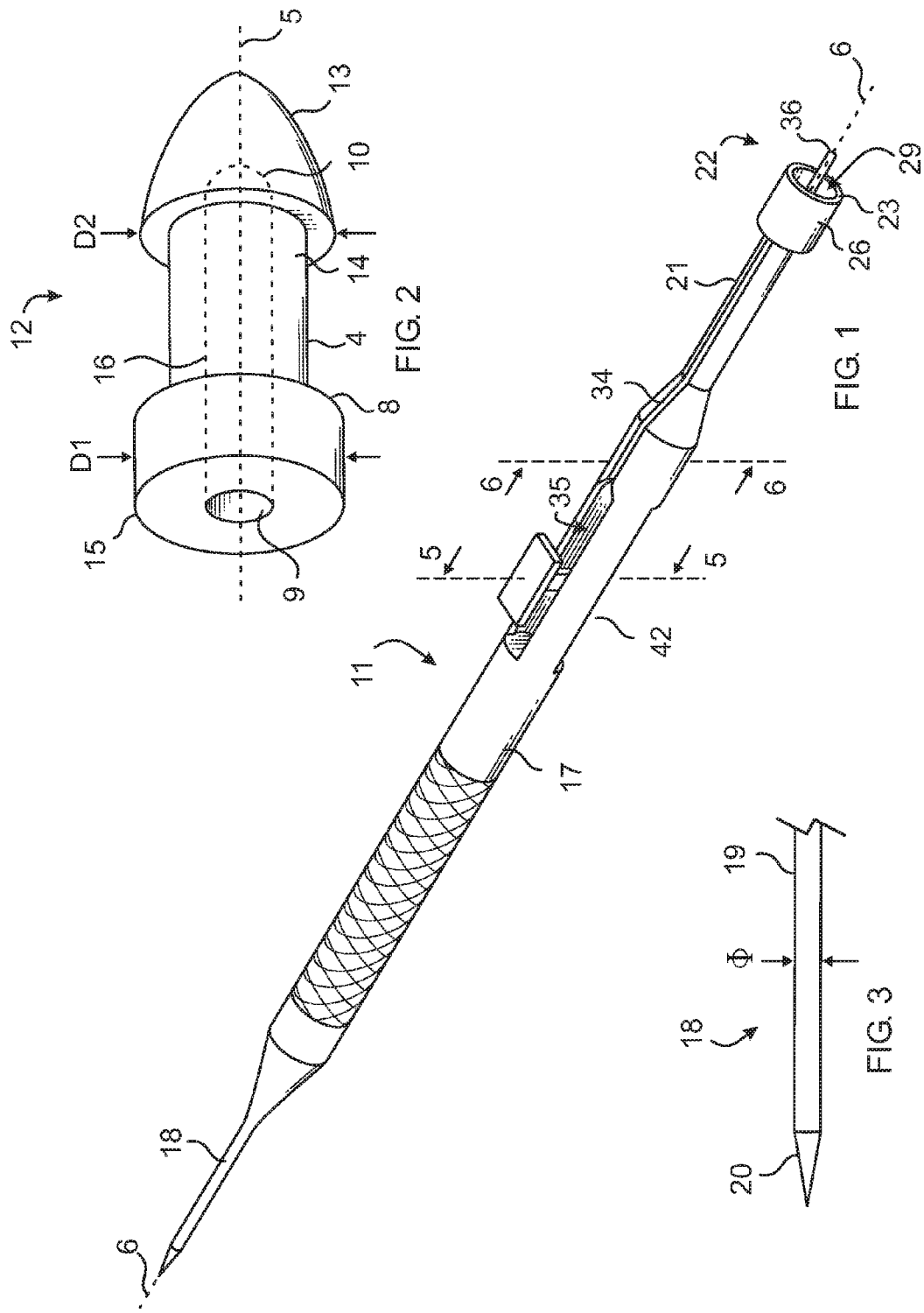

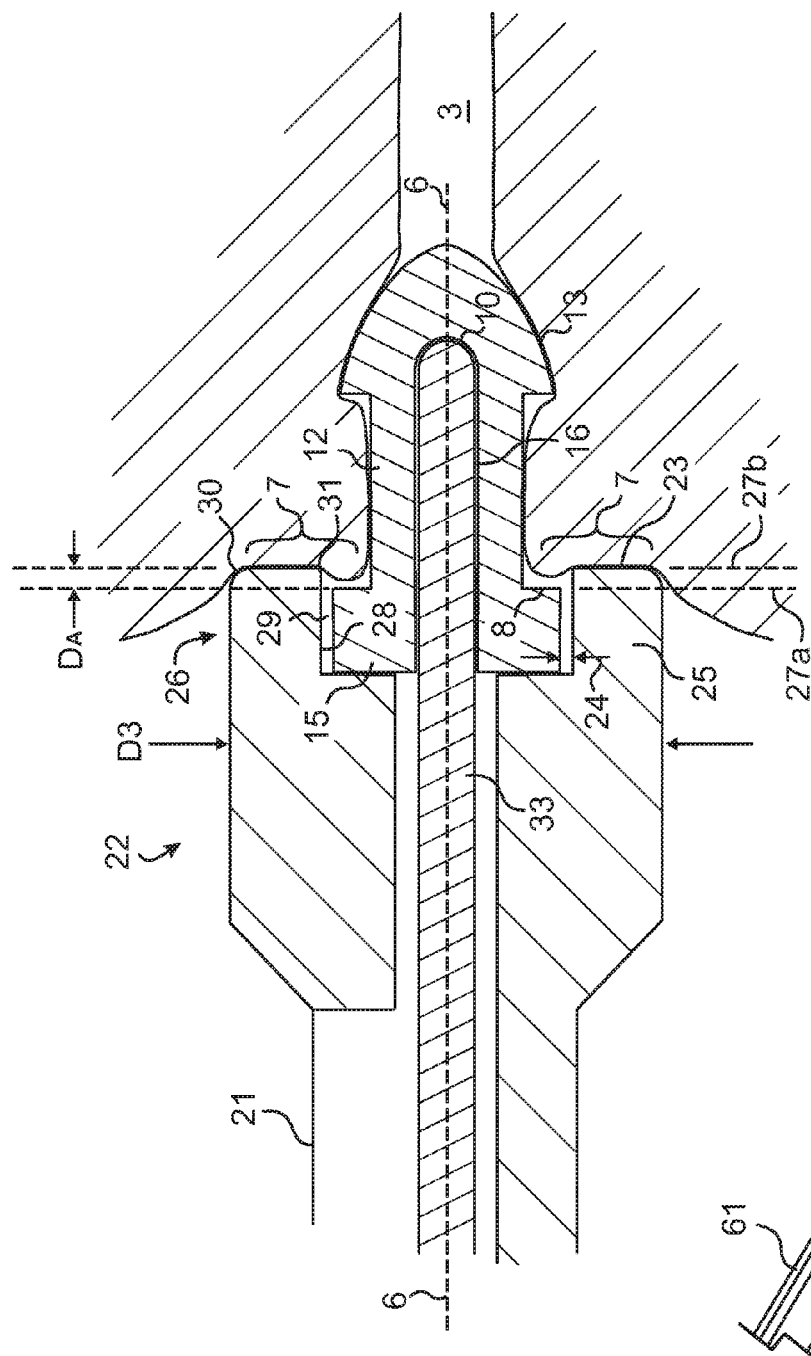
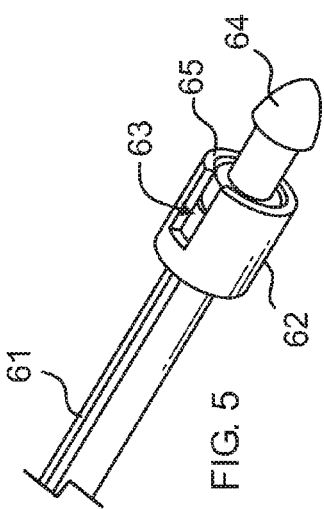
FIG. 4
FIG. 5

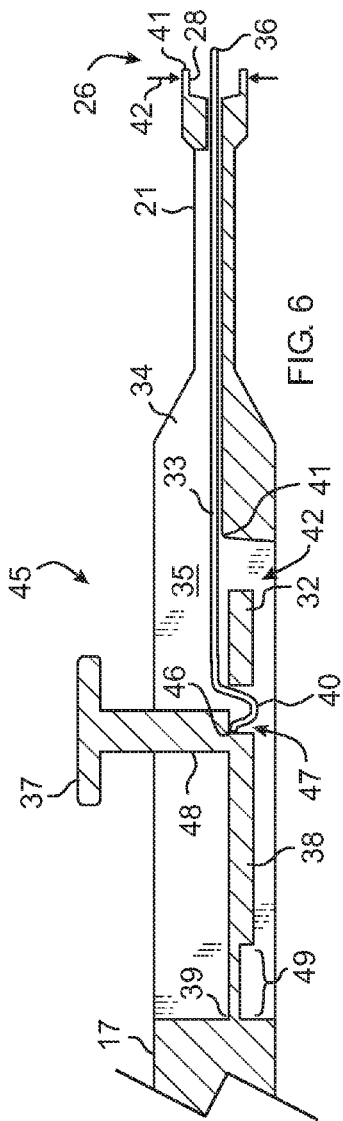
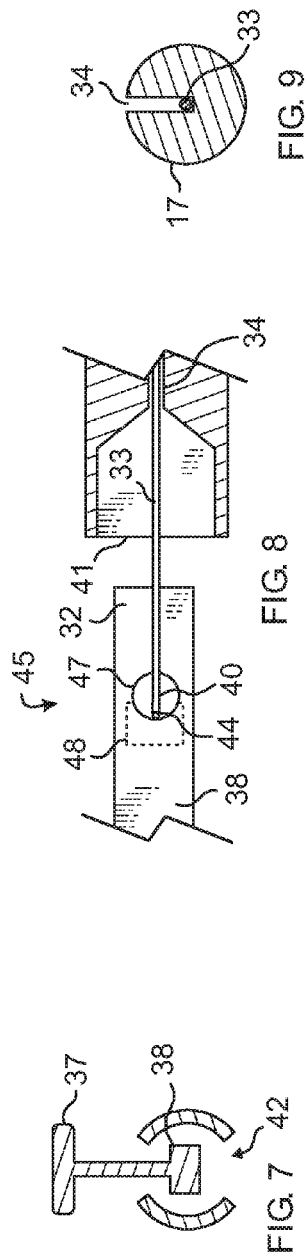
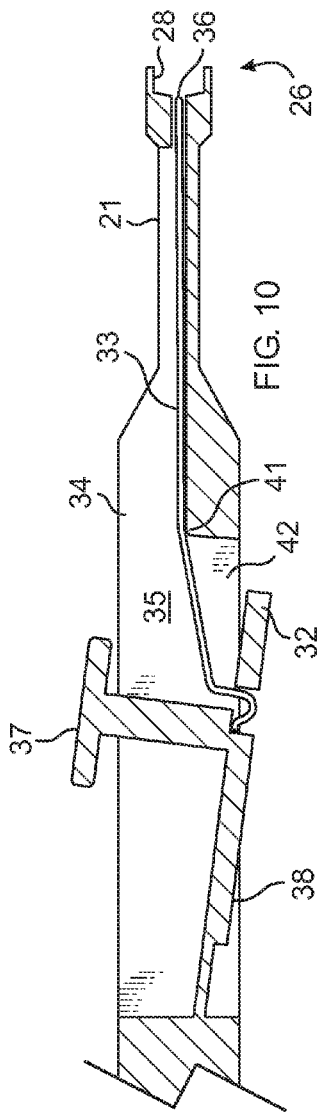

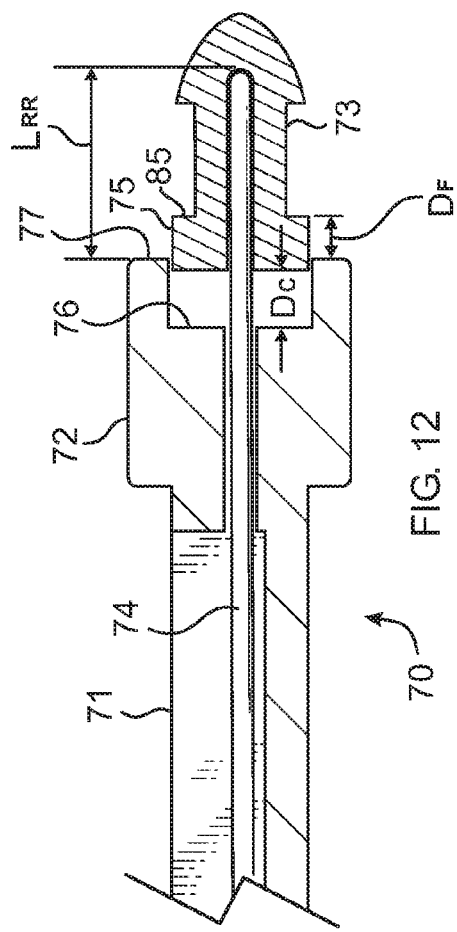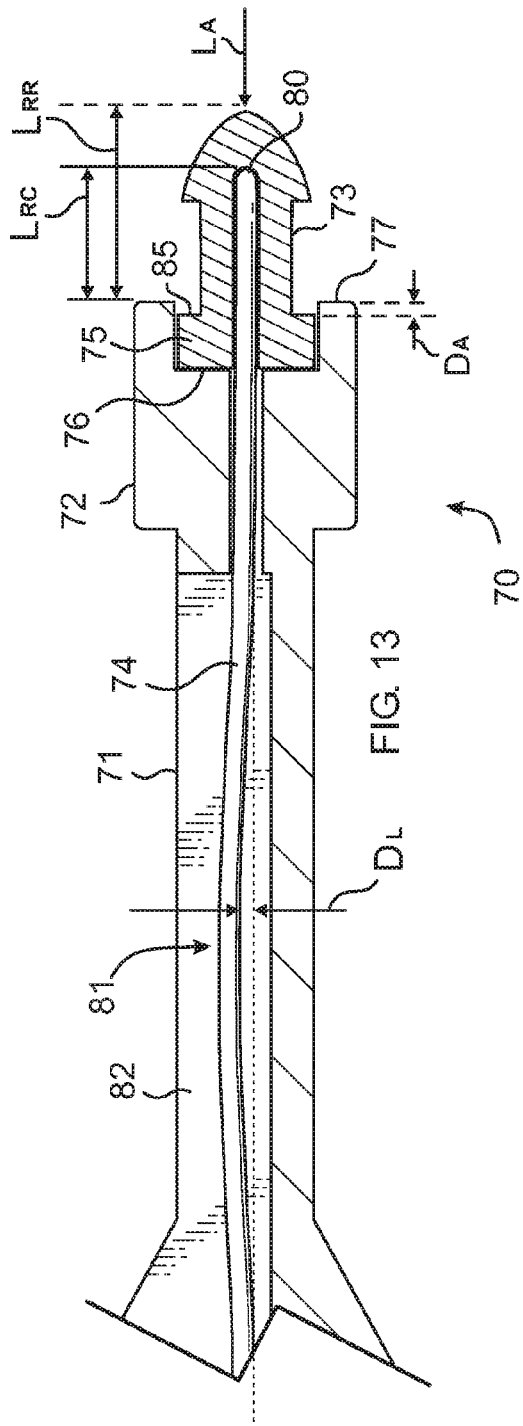

PUNCTAL PLUG INSERTER AND METHOD

FIELD OF THE INVENTION

This invention relates to surgical implements and more specifically to instruments used in the treatment and repair of meati, particularly naso-lacrimal canaliculi and puncta.

BACKGROUND

Dry eye syndrome which usually results from inadequate production of the aqueous layer of tears can often be palliated by obstructing the punctum that drain tears into the nose. This is done by means of minuscule punctal spiles or plugs. Each plug features a distal glanduliform or barbed head. The head acts as an anchor and is backed by a short median shank of a cross-diameter substantially smaller than the largest portion of the head, and a broad circular cap which remains outside the punctum and can be seized with tweezers or pincers to extract the plug. The largest cross-diameter of the head must be slightly larger than the cross-diameter of the canaliculus and its opening punctum in order to maintain the plug in its optimal position.

The prior art offers an ophthalmic punctal opening dilatation and plug insertion tool available under the name Ready-Set Punctum Plug from FCI Opthalmics of Marshfield Hills, Mass. which consists of a pencil dimensioned member having at one end a dilating reamer and at the opposite end a thin shaft through which runs a small axially translatable rod. The distal extremity of the rod protrudes slightly from the end of the shaft and is sized to penetrate a small axial bore in the proximal face of the cap and thus hold the plug during its insertion into the punctal opening of a canaliculus or other type of meatus. A bi-directional squeeze mechanism in the median portion of the tool withdraws the rod and releases the plug once it has reached the desired position.

The prior art tool suffers from several critical drawbacks.

First, the dilating reamer is constituted by circular shaft of a substantial cross-diameter terminated by an elongated conical spike. The degree of penetration of the spike into a meatus determines the amount of obtained dilation. Although such a dilator has the flexibility of providing an adjustable amount of dilatation, the physician can only estimate how far to push the dilator into the punctal opening. If the dilatation is not sufficient, the insertion of the plug may be painfully difficult or impossible. If the dilatation exceeds the diameter of the cap, the plug may be inadvertently pushed too far into the canaliculus. If the dilatation even exceeds the largest diameter of the anchoring head, the plug may be too loose and soon exit the meatus.

Second, because of the relatively large forces typically required to insert the typically tight-fitting plug, it can be difficult for the physician to judge whether the plug is located at the proper optimum depth with respect to the punctum. Plugs which have been inserted too deeply can be difficult to remove, leading to tissue damage, infections or other complications.

Third, the prior art bi-directional squeeze mechanism for retracting the rod is located on a part of the tool that the physician will typically need to grasp during insertion. Therefore, when the physician grasps this portion and applies force to the tool to insert the plug through the punctum, it is possible for the physician to inadvertently actuate the squeeze mechanism and prematurely release, or partially dislodge the plug from the tool. Further, because the squeeze mechanism typically requires that the physician's thumb and index finger be located on opposite sides of the mechanism in order to actuate withdrawal of the rod, control of the tool, especially under force is made difficult.

In addition, the precarious holding of the plug by the small amount of the rod that penetrates the cap may not allow the physician much freedom of action during the insertion process, and often results in the inadvertent, premature separation of the sterile plug from the tool. The plug may be dropped before insertion or left only partially inserted. In the latter instance, another tool must be used to extract the partially inserted plug and re-attach it to the insertion tip in order to attempt a repeat of the insertion procedure. Such procedures can be difficult and time-consuming.

Therefore, there is a need for a punctal plug insertion device and method which addresses one or more of the above problems.

SUMMARY

The principal and secondary objects of the invention are to provide improved treatment of meati.

These and other objects are achieved by an inserter tool having greater controllability. In some embodiments there is provided a tool which overcomes the above-described shortcomings by providing an improved ophthalmic instrument for dilating a punctum and safely and accurately inserting a plug, in which the cross-diameter of the meatus-dilating shaft is calibrated to the desired size. In some embodiments there is provided a tool having a cup having an internal geometry commensurate with the external shape and size of the cap is axially mounted at the end of the plug inserting shaft for securely holding and directing the plug during the insertion procedure.

In some embodiments there is provided a surgical tool for inserting a plug into the punctal opening of a meatus having a given diameter, wherein said plug comprises a body elongated along a first axis, said body having a distal insertable portion, and a proximal cap having a distal flange surface oriented to rest against tissue surrounding said opening when properly inserted, said tool comprising: a median member having a proximal end, a distal end, and an elongated tip projecting from said distal end; a holder for releasably securing said plug to said tip; and, an insertion-resisting bearing surface located at an axial position coplanar with or distal to said flange surface when said plug is properly positioned within said meatus.

In some embodiments said holder comprises: a cup terminating said tip and being axially aligned with said tip; and wherein said cup has an internal geometry commensurate with said cap.

In some embodiments said cup is made from a resiliently flexible, translucent material.

In some embodiments said cap is spaced an axial distance apart from said cup.

In some embodiments said distance is eliminated when said plug is placed under a given axial mechanical load.

In some embodiments said insertable portion has a largest cross-diameter slightly larger than said given diameter; wherein said plug has an axial bore; and wherein said tool further comprises a rod running axially within said tip and cup and having a distal extremity removably insertable into said bore.

In some embodiments said tool further comprises a unidirectionally activated withdrawing mechanism housed in a cavity within said member; wherein said withdrawing mechanism is configured to manually cause withdrawal of said distal extremity from said cup.

In some embodiments said withdrawing mechanism comprises: a deflectable beam within said cavity; a pushbutton acting upon said beam; and said rod having a proximal extremity secured to said beam.

In some embodiments said beam is resiliently deflectable and said rod is resiliently deformable.

In some embodiments said rod is permanently deformable.

In some embodiments said tool further comprises a radial slot extending axially along said median member, wherein said slot is shaped and dimensioned to allow for said rod to form a radial bow within said slot when said rod is placed under a given axial mechanical compression load.

In some embodiments a distal extremity of said rod retracts axially under a given axial mechanical compression load.

In some embodiments the tool further comprises a punctum and meatus dilator projecting axially from an end of said member opposite said tip, wherein said dilator is dimensioned according to one of a plural number of sizes for said plug.

In some embodiments said dilator comprises: a cylindrical stem having a cross-diameter substantially equal to the cross-diameter of said insertable portion; and a conical spike terminating said stem.

In some embodiments there is provided that in a surgical tool for inserting a plug into the opening punctum of a meatus, wherein said plug includes a cap at a proximal end having a distal flange surface oriented to rest against tissue surrounding said opening, an improvement which comprises: a holder for releasably securing said plug to said tool; and, an insertion-resisting bearing surface located at an axial position commensurate with or distal to said flange surface when said plug is properly positioned within said meatus.

In some embodiments the cap of said plug has a central, axial bore in a proximal face of said cap, and said tool further includes an axial rod extending through said holder and being sized to intimately penetrate said bore, and wherein said improvement further comprises said rod having an extremity translatable in and out of said holder.

In some embodiments said holder comprises a distally open-ended cup structure made from a resiliently flexible, translucent material.

In some embodiments said cap is spaced an axial distance apart from said cup structure.

In some embodiments there is provided that in a surgical tool for inserting a plug into the opening punctum of a meatus, an improvement which comprises a cylindrical stem having a cross-diameter commensurate with said plug and a conical spike terminating said stem.

In some embodiments there is provided a method for seating a plug in the punctum of a patient, wherein said plug has a proximal cap having a flange surface for resting against the tissue surrounding said punctum, said method comprises: selecting an oblong inserter tool having a first end releasably carrying a punctal plug thereon, and a penetration-preventing bearing surface; pushing said tool axially until a contact is made between said bearing surface and a portion of tissue surrounding said punctum; detecting an increase in resistance to further axial pushing while said contact is maintained; stopping further axial pushing in response to said detecting; releasing said plug from said tool; and, axially pulling said tool away from said plug.

In some embodiments said releasing comprises axially retracting a deformable rod from an axial bore in said plug.

In some embodiments the method further comprises prior to said pushing, inserting a pre-sized dilator located on said tool into said punctum, wherein said dilator is dimensioned according to one of a plural number of sizes for said plug.

In some embodiments the method further comprises: carrying said plug where said flange surface is located in a first position an axial distance apart from said bearing surface; and wherein said pushing comprises: allowing said cap to retract proximally when said plug is placed under a given axial mechanical load, so that said axial distance is eliminated and said flange surface is located substantially coplanar with said bearing surface.

In some embodiments there is provided a combination of a punctal plug and a tool for inserting said plug into the punctal opening of a meatus; wherein said plug comprises: a body elongated along a first axis; a distal insertable portion; a proximal cap having a distal flange surface oriented to rest against tissue surrounding said opening when said plug is properly emplaced in said meatus; and, wherein said tool comprises: a median member having a proximal end, a distal end, and an elongated tip projecting from said distal end; a holder for releasably securing said plug to said tip; an insertion-resisting bearing surface located at an axial position to resist penetration of said flange surface through said punctum.

In some embodiments said bearing surface and said flange surface are substantially coplanar.

In some embodiments said holder comprises: a cup terminating said tip and being axially aligned with said tip; and wherein said cup has an internal geometry commensurate with said cap.

In some embodiments said bearing surface continuously surrounds said flange surface.

In some embodiments said cap is retractably secured to said holder between an extended position and a retracted position and wherein axial position is substantially coplanar with said distal flange surface when said cap is in said retracted position.

The content of the original claims is incorporated herein by reference as summarizing features in one or more exemplary embodiments.

BRIEF DESCRIPTION OF THE DRAWINGS

FIG. 1 is a perspective view of a plug-inserting and meatus-dilating tool according to an exemplary embodiment of the invention.

FIG. 2 is a perspective view of a plug.

FIG. 3 is a partial side view of a meatus-dilating portion of the tool.

FIG. 4 is diagrammatic partial cross-sectional side view of the tool of FIG. 1 shown during plug insertion through the punctum.

FIG. 5 is diagrammatic partial perspective view of an alternate embodiment of the tool having a viewing notch through the cup structure.

FIG. 6 is diagrammatic partial cross-sectional side view of the tool of FIG. 1 shown in the plug-holding position.

FIG. 7 is a cross-sectional view taken along line 5-5 of FIG. 1.

FIG. 8 is a cross-sectional view taken along line 6-6 of FIG. 1.

FIG. 9 is a diagrammatic partial top view of the tool of FIG. 1 showing the rod engaging the deflectable beam.

FIG. 10 is diagrammatic partial cross-sectional side view of the tool of FIG. 1 shown in the plug-releasing position.

FIG. 12 is diagrammatic partial cross-sectional side view of an alternate embodiment of the tool having a retractably carried plug in a mechanically unloaded condition.

FIG. 13 is diagrammatic partial cross-sectional side view of the tool of FIG. 10 while under a given axial mechanical load.

DESCRIPTION OF THE EXEMPLARY EMBODIMENTS

Figure 11:
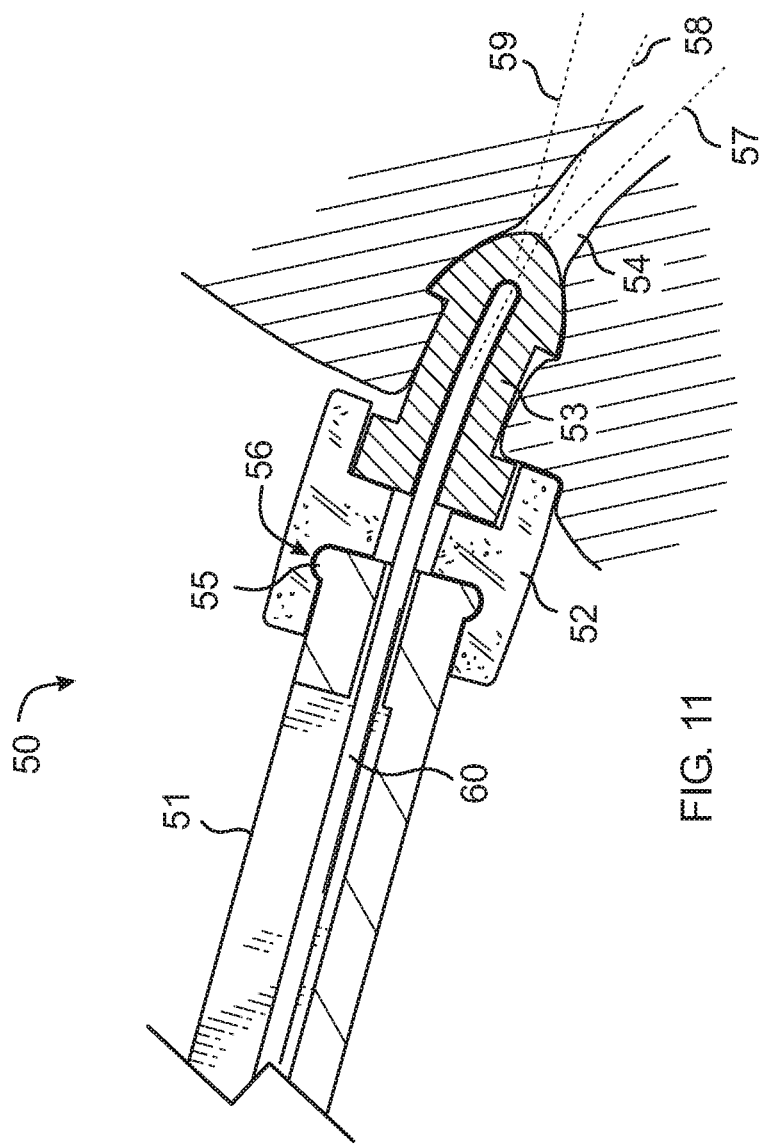
FIG. 11 is diagrammatic partial cross-sectional side view of an alternate embodiment of the tool having a resiliently deformable plug-carrying structure.

Referring now to the drawing, there is shown in FIGS. 1-4 a surgical tool 11 according to an exemplary embodiment of the invention and specifically adapted to install a spile or plug 12, about 1.5 millimeters in axial length, through the punctal opening of a lacrimal canaliculus meatus 3.

In this example, as shown in FIG. 2, the punctal plug 12 comprises a body 4 made of a unitary piece of sterile, resiliently deformable, biocompatible material such as silicone, elongated along an axis 5. The body has a distal bulb or glanduliform, that is a barbed head 13. The head has a largest cross-diameter D2 slightly larger than the internal cross-diameter of the host meatus in order to be retained in position therein. Thus, it can be forcefully inserted through the punctum and held securely in a canaliculus or other type of meatus. The head is backed by a narrow cylindrical shank 14 terminating in a proximal substantially cylindrical cap 15 having a cross-diameter D1 larger than the shank and typically larger than the largest cross-diameter D2 of the head.

The cap 15 therefore terminates in a distal flange surface 8 which is oriented to rest against the zone of tissue 7 surrounding the punctal opening when the plug 12 is properly emplaced in the meatus 3. A central, axial bore 16 extends through the plug from a circular opening 9 in the proximal face of the cap, through the shank 14, and terminating at a closed end 10 within the head 13. Thus, the plug 12 can be inserted through the punctal opening of a meatus with the cap 15 remaining on the outside. The plug can eventually be removed by grabbing it with tweezers or pincers.

The meatus-dilating and plug-inserting tool 11 comprises an oblong pencil-shaped and dimensioned member 17 having a major axis 6. A punctum and meatus-dilating portion 18, as illustrated in FIG. 3, is about 20 millimeters in axial length and consists of a cylindrical stem 19 terminating into a pointed conical spike 20 which projects axially from a first, proximal end of the member. The spike can be sharp or semi-sharp. The cross diameter Φ of the stem is calibrated to reflect the cross-diameter of desired meatus opening. The physician can thus introduce the punctum and meatus-dilating portion 18 through a punctal opening and into a meatus to size them according to the dimensions of the plug. Thus, a differently sized plug can be provided pre-loaded on a tool having an appropriately sized dilating portion for a single use. In other words, the dilator can be dimensioned according to one of a plural number of sizes for said plug. With such a pre-sized dilator, the physician can simply insert the dilator beyond the spike in order to properly dilate the punctum and meatus.

A shaft 21, about 30 millimeters long, projects axially from the opposite, distal end of the tool member 17 and is distally terminated by a structure 22 which both carries the plug 12 during insertion and provides a penetration-resisting bearing surface 23 sized, shaped, dimensioned, and located to resist and in most cases prevent over-penetration of the plug through the punctum during insertion.

As shown in FIG. 4, the insertion-resisting bearing surface 23 is located at an axial position coplanar with or distal to the distal flange surface 8 of the plug 12 when the plug is properly positioned within the meatus so that the distal flange surface rests against a zone of tissue 7 surrounding the punctum. At this location the bearing surface contacts and bears against the zone preventing penetration of the cap 15 into the meatus 3. The bearing surface is oriented to face in substantially the distal direction which is substantially the same direction as the distal flange surface.

In other words, the bearing surface 23 can be said to be substantially adjacent to the distal flange surface 8. The word "substantially" is used because minor axial and radial separation may exist between the distal flange surface and the bearing surface when the tool is at rest and when subject to the forces of insertion as will be described in greater detail below. For example, in this embodiment a small gap 24 can be found between the radially inner extent of the bearing surface and the radially outer extent of the flange surface so that the plug can easily disengage from the structure. Further, both the distal flange surface and the bearing surface can be substantially planar and fall within planes 27a and 27b respectively. The substantially parallel planes can be separated a minor axial distance $D_A$ while remaining substantially axially and radially adjacent and substantially coplanar.

The bearing surface 23 in the present embodiment is supported by a radial prominence 25 formed by a distally located open-ended cup structure 26. The substantially cylindrical cup 26 is oriented substantially coaxially with the major axis 6 of the shaft 21. The cup has a generally axially cylindrical wall 28 terminating a substantially circular distal rim which forms the penetration-resisting bearing surface 23 circumferentially surrounding a substantially circular distal opening to a substantially cylindrical internal cavity 29 and extending radially beyond the radial extent of the cap 15 thus leaving the small annular gap 24. Thus the distal opening of the cup is constantly large enough to allow axial passage of the cap therethrough.

In this embodiment, the axial location of the bearing surface 23 is selected to be slightly distal to the flange surface 8. In other words, the shape of the bearing surface is selected to be substantially planar and located within a plane 27a substantially perpendicular to the major axis 6 of the cup 26 and separated an axial distance $D_A$ from the substantially planar and substantially parallel flange surface 8. Alternately, the two surfaces can be exactly or essentially coplanar.

The diameter D3 of the cup 26 is selected to provide adequate surface area in order to prevent penetration of the cup through the punctum but not be so large as to obscure the view of the plug 12 during insertion. Thus, the diameter is preferably between about 1.01 and 3 times the diameter D2 of the cap 15, and more preferably between about 1.1 and 1.8 times the diameter of the cap. In this way, the forces of the bearing surface 23 against the tissues surrounding the punctum are evenly distributed during plug placement enhancing axial alignment of the plug 12 with the meatus 3.

In this embodiment, the radially distal lip 30 and the radially proximal lip 31 of the rim of the cup 26 are rounded to afford additional comfort. In this embodiment, the internal geometry of the cup is selected to substantially match the outline of the cap 15 at the proximal end of the plug. In other words, the cup is commensurate with the outline of the cap.

In this embodiment the bearing surface 23 completely and continuously surrounds the distal flange surface 8. However, interruptions in the continuity of the bearing surface can occur without departing from its penetration preventing function. For example, in FIG. 5 there is shown the distal end of a shaft 61 having a cup structure 62 adapted to have a top notch 63 which allows the physician to view a portion of the plug 64 therethrough. The presence of the notch also creates a discontinuity in the bearing surface 65. The dimensions of the discontinuity can be minimized to keep an adequate surface area of the bearing surface for contacting the tissues surrounding the punctum and preventing over-insertion of the plug.

Referring primarily now to FIGS. 6-10, a thin rod 33 in the form of a resiliently flexible steel wire runs from the cup 26 within a slot 34 to a cavity 35 in a median part of the tool member 17. The distal extremity 36 of the rod is sized to intimately penetrate the bore 16, about 0.25 millimeter in diameter, in the plug 12 and, in this embodiment, hold the cap 15 within the cup and the whole plug at the distal end of the shaft 21 during the insertion process.

A uni-directionally activated rod-withdrawing mechanism 45 housed in the cavity 35 and activated by a pushbutton 37 translates the rod 33 from its plug-holding position shown in FIG. 6 to a plug-disengaged, plug-releasing position shown in FIG. 10. The mechanism consists of the pushbutton acting on a deflectable beam 38 fixedly secured at one end 39 to the core of the tool member 17 and tied at its other distal end 32 to the proximal extremity of the rod. The proximal extremity of the rod is formed into an upturned hook structure 40 which dips through a vertical hole 47 formed through the beam. The hole is partially overlapped by a portion of the pushbutton post 48 where it connects to the beam. This creates a crook 46 which is engaged by the proximal tip 44 of the hook structure. This structure provides an easily assembled anchorment between the proximal extremity of the rod and the beam. The beam can have a thinned portion 49 near the end 39 secured to the tool to adjust the force necessary to cause deflection.

In one embodiment the beam 38 can be resiliently deflectable and the rod 33 resiliently deformable so that when the button 37 is released, the beam resiliently returns to its undeflected state and the rod returns to its un-deformed state. In this way, the release of the button can cause the distal extremity 36 of the rod to re-engage into the axial bore 16 of the plug 12 and allow the physician to reposition the plug if desired. Alternately, the rod can be substantially permanently deformable so that release of the button does not cause the distal extremity to re-extend distally toward the plug. In this way, there is no chance that the distal extremity of the rod will re-engage the bore 16 in the plug.

As shown in FIG. 10, when the pushbutton 37 is depressed, the beam 38 deflects and pulls the rod 33 against the shoulder 41 at the intersection of the slot 34 and cavity 35 causing the rod to slightly translate proximally out of the cup 26 and thus the cap 15 allowing the plug 12 to be released from the cup. A cutout 42 in the wall of the cavity opposite the pushbutton provides clearance for the downward movement of the distal end 32 of the beam.

The plug can thus be conveniently mounted at the distal end of the shaft 21 and have its cap 15 held into the cup 26 by the distal extremity 36 of the rod 33. The physician can then insert the plug up to, but exclusively of the cap into the punctal opening of a meatus. Pressing the pushbutton 37 liberates the plug 12 from the tip and allows for the withdrawal of the tool.

Referring now to FIG. 11, there is shown an alternate embodiment of the tool 50 having a distally projecting shaft 51. A cup 52 made from silicone, polyurethane, Teflon brand material, ethylene, propylene or other a sterile, resiliently deformable, biocompatible, and translucent material is mounted to the distal end of the shaft. The mounting of the cup to the shaft is made more robust by a circumferential bead 55 engaging a corresponding circumferential groove 56 in the cup. Optionally, a layer of adhesive can be used between some of the surfaces of the shaft contacting the cup to more securely bond the cup to the shaft.

The cup 52 being made from a resiliently deformable material allows for enhanced comfort during placement of the plug through the patient's punctum. It also allows the major axis 58 of the plug 53 to deflect toward the axis 57 of the meatus 54 when the major axis 59 of the tool is angularly misaligned with the meatus. It shall be noted that the rod 60 can be dimensioned to allow for the flexible deflection of the rod and plug. This deflectability allows for a more rapid, comfortable, and accurate insertion. The cup being made from a translucent material allows the physician to better view the plug and punctum during emplacement.

Referring now to FIGS. 12-13, there is shown an alternate embodiment of the tool 70 having a distally projecting shaft 71 supporting a coaxially oriented distal cup structure 72 for carrying and orienting a punctal plug 73. In this embodiment the plug is carried distally further out on the tool so that the physician can better see the plug during insertion.

As shown in FIG. 12, when the plug 73 is fully engaged upon the retractable rod 74 and while the plug and rod are at rest under no applied axial mechanical load, the plug is located in a distally extended position where its cap 75 is spaced apart an axial distance $D_C$ from the proximal floor 76 of the cup. Consequently, the flange surface 85 of the cap is located a distance $D_F$ from the distal rim 77 of the cup which forms the penetration-resisting bearing surface. In this "at rest" position the rod 74 extends distally beyond the distal rim 77 of the cup by an axial length $L_{RR}$.

As shown in FIG. 13, during installation of the plug into the meatus, an external mechanical load is applied. An axial component $L_A$ of that load can cause the distal extremity 80 of the rod 74 to retract slightly proximally, thus causing the rod to form a bow 81 in the slot 82 of the tool. In other words, the flexibility of the rod is selected to allow for the bow of the rod to deflect radially a distance $D_L$ within the slot when placed under an axial compression load. The load on the rod occurs when the plug is inserted in the meatus and the flange surface 85 of the plug 73 contacts the tissue surrounding the punctum and the resistance to further insertion increases. It is important to note that the mechanical properties of the rod and the plug must be selected to prevent penetration of the cap of the plug through the punctum. In other words the rod cannot be so stiff that is fails to retract slightly under the insertion force when the flange comes into contact with the tissue surrounding the punctum.

It shall be noted that the bowing of the rod 74 will cause the cap 75 of the plug to travel proximally so that it retracts within the internal cavity of the cup structure 72 until the proximal surface of the cap bears against the proximal floor 76 of the of the cup. The distal flange surface 85 of the plug will then be substantially coplanar with the distal rim 77 of the cup, thus acting as the penetration-resisting bearing surface as described above in connection with an earlier embodiment. This helps prevent further insertion of the plug into the meatus. Similarly to a previous embodiment, the word "substantially" is used because the distal flange surface 85 may be located a minor axial distance $D_A$ from the bearing surface 77.

Selecting the rod 74 to have a certain rigidity allows the physician to gauge how much axial force is being applied, by detecting whether and to what extent the rod has begun to bow and the plug has begun to retract, thereby providing feedback to the physician. For most typical punctal plug installation applications the rod can be selected to be between about 0.1 millimeter and 0.4 millimeter in diameter to allow for retraction during application of the maximum axial force during insertion.

Figure 14:
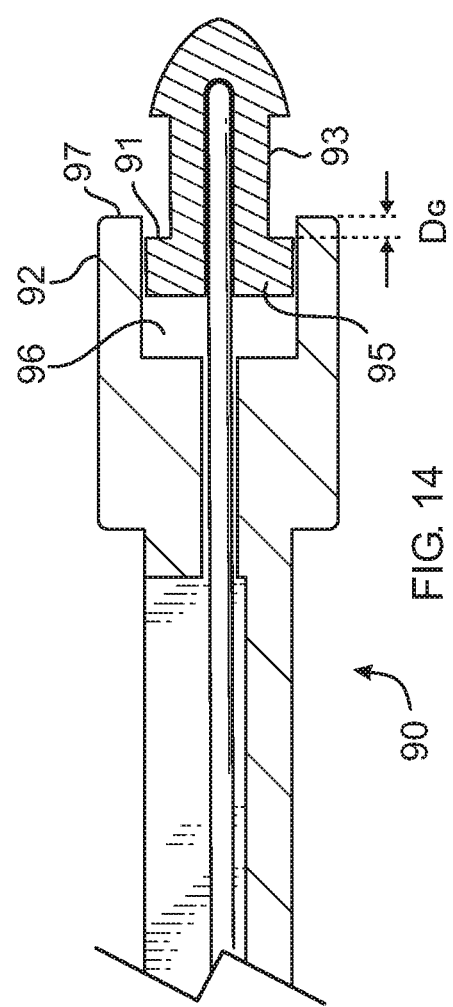
FIG. 14 is diagrammatic partial cross-sectional side view of an alternate embodiment of the tool having a retractably carried plug in a mechanically unloaded condition with its cap fully recessed within the tool cup.

Referring now to FIG. 14 there is shown an alternate embodiment of the tool 90 similar to the tool of FIG. 13, however, in this embodiment the distal rim 97 of the coaxially oriented distal cup structure 92 is extended, and the internal cavity 96 made deeper so that while the tool is in its "at rest" state without an axial force applied, the punctal plug 93 is carried so that its cap 95 is fully contained in the cup. Thus, the distal rim 97 is located a distance DG axially distal from the distal flange surface 91 of the plug. In this embodiment there is always at least some amount of setback of the flange surface from the bearing surface so that over-insertion is prevented especially in those cases where the meatus is found to be overly dilated or otherwise looser than expected and the plug does not retract as expected when the axial force is applied.

While the exemplary embodiments of the invention have been described, modifications can be made and other embodiments may be devised without departing from the spirit of the invention and the scope of the appended claims.

What is claimed is:

1. The combination of a punctal plug and a tool for inserting said plug into the punctal opening of a meatus having a given diameter,
    wherein said plug comprises:
        a distal insertable head portion backed by a shank terminating in a proximal cap having a distal flange surface oriented to rest against tissue surrounding said opening when properly inserted;
    wherein said tool comprises:
        a median member having a proximal end, a distal end, and an elongated tip projecting from said distal end;
        a holder for releasably securing said plug to said tip, said holder comprising:
            a cup having an internal geometry commensurate with said cap and a distal opening constantly large enough to allow axial passage of said cap therethrough; and,
            an insertion-resisting bearing surface surrounding said distal opening;
            a notch in a wall of said cup exposing a view of said cap when said tool is at rest with said plug engaged thereon, and said bearing surface being located at an axial position coplanar with or distal to said flange surface when said plug is properly positioned within said meatus, and visibly exposing a medial portion of said shank when said tool is at rest with a plug engaged thereon.

2. The combination of claim 1, wherein said cup is axially aligned with said tip;
    wherein said cap has a first diameter;
    wherein said cup has a second diameter between about 1.1 and 1.8 times said first diameter, thereby avoiding obscuring a view of said plug during insertion.

3. The combination of claim 2, wherein said cup is made from a resiliently flexible, translucent material.

4. The combination of claim 2, wherein said cup is further dimensioned so that said cup is spaced an axial distance apart from said cap.

5. The combination of claim 4, wherein said distance is eliminated when said plug is placed under a given axial mechanical load.

6. The combination of claim 2,
    wherein said tool further comprises a rod running axially within said tip and cup and having a distal extremity removably insertable into said plug.

7. The combination of claim 6, which further comprises a uni-directionally activated withdrawing mechanism housed in a cavity within said member; wherein said withdrawing mechanism is configured to manually cause withdrawal of said distal extremity from said cup.

8. The combination of claim 7, wherein said withdrawing mechanism comprises:
    a deflectable beam within said cavity;
    a pushbutton acting upon said beam; and
    said rod having a proximal extremity secured to said beam.

9. The combination of claim 8, wherein said beam is resiliently deflectable and said rod is resiliently deformable.

10. The combination of claim 8, wherein said rod is permanently deformable.

11. The combination of claim 8, wherein said tool further comprises a radial slot extending axially along said median member, wherein said slot is shaped and dimensioned to allow for said rod to form a radial bow within said slot when said rod is placed under a given axial mechanical compression load.

12. The combination of claim 8, wherein a distal extremity of said rod retracts axially under a given axial mechanical compression load.

13. The combination of claim 1, which further comprises a punctum and meatus dilator projecting axially from an end of said member opposite said tip, wherein said dilator is dimensioned according to one of a plural number of sizes for said plug.

14. The combination of claim 13, wherein said dilator comprises:
    a cylindrical stem having a cross-diameter substantially equal to the cross-diameter of said insertable portion; and
    a conical spike terminating said stem.

15. In a surgical tool for inserting a plug into the opening punctum of a meatus, wherein said plug includes a cap at a proximal end of a shank, said cap having a distal flange surface oriented to rest against tissue surrounding said opening, an improvement which comprises:
    a holder for releasably securing said plug to said tool, said holder comprising:
        a cup having an internal geometry commensurate with said cap and a distal opening constantly large enough to allow axial passage of said cap therethrough; and
        a notch in a wall of said cup exposing a view of said cap when said tool is at rest with said plug engaged thereon; and,
    an insertion-resisting bearing surface surrounding said flange surface, and said bearing surface being located at an axial position commensurate with or distal to said flange surface when said plug is properly positioned within said meatus, and visibly exposing a medial portion of said shank when said tool is at rest with a plug engaged thereon.

16. In the surgical tool of claim 15, wherein said tool further includes an axial rod extending through said holder and being sized to intimately penetrate said plug, and wherein said improvement further comprises said rod having an extremity translatable in and out of said holder.

17. The improvement of claim 16, wherein said cup is made from a resiliently flexible, translucent material.

18. The improvement of claim 17, wherein said cup is further dimensioned so that said cap is spaced an axial distance apart from said cup structure.

19. A method for seating a plug in the punctum of a patient, wherein said plug has a shank terminating in a proximal cap having a flange surface for resting against the tissue surrounding said punctum, said method comprises:
- selecting an oblong inserter tool having a first end having a open-ended cup releasably carrying a punctal plug thereon, wherein said cup has a distal opening constantly large enough to allow axial passage of said plug therethrough, and a penetration-preventing bearing surface surrounding said plug;
- pushing said tool axially until a contact is made between said bearing surface and a portion of tissue surrounding said punctum;
- viewing said shank and said cap during said pushing;
- detecting an increase in resistance to further axial pushing while said contact is maintained;
- stopping further axial pushing in response to said detecting;
- releasing said plug from said tool through a distal opening of said cup; and,
- axially pulling said tool away from said plug.

20. The method of claim 19, wherein said releasing comprises axially retracting a deformable rod from an axial bore in said plug.

21. The method of claim 19, which further comprises prior to said pushing, inserting a pre-sized dilator located on said tool into said punctum, wherein said dilator is dimensioned according to one of a plural number of sizes for said plug.

22. The method of claim 19, which further comprises:
- carrying said plug where said flange surface is located in a first position an axial distance apart from said bearing surface;
- and wherein said pushing comprises:
  - allowing said cap to retract proximally when said plug is placed under a given axial mechanical load, so that said axial distance is eliminated and said flange surface is located substantially coplanar with said bearing surface.

23. The combination of a punctal plug and a tool for inserting said plug into the punctal opening of a meatus;
- wherein said plug comprises:
  - a body elongated along a first axis;
  - said body including a shank;
  - a distal insertable head portion backed by said shank;
  - said shank terminating in a proximal cap having a distal flange surface oriented to rest against tissue surrounding said opening when said plug is properly emplaced in said meatus; and,
- wherein said tool comprises:
  - a median member having a proximal end, a distal end, and an elongated tip projecting from said distal end;
  - a holder for releasably securing said plug to said tip;
  - said holder comprising:
    - a cup having an internal geometry commensurate with said cap and a distal opening constantly large enough to allow axial passage of said cap therethrough; and
    - a notch in a wall of said cup exposing a view of said cap when said tool is at rest with said plug engaged thereon; and,
    - an insertion-resisting bearing surface located at an axial position to resist penetration of said flange surface through said punctum, and visibly expose a medial portion of said shank when said tool is at rest with a plug engaged thereon;
- wherein said bearing surface surrounds said flange surface.

24. The combination of claim 23, wherein said bearing surface and said flange surface are substantially coplanar.

25. The combination of claim 23, wherein said cup is axially aligned with said tip.

26. The combination of claim 23, wherein said cap is retractably secured to said holder between an extended position and a retracted position and wherein an axial position of said insertion-resisting bearing surface is substantially coplanar with said distal flange surface when said cap is in said retracted position.

* * * * *